United States Patent [19]
>
> Yamamoto et al.

[11] 4,018,818

[45] Apr. 19, 1977

[54] HYDROXYL-SUBSTITUTED 2-CHLORO-α-(TERT-BUTYLAMINOMETHYL)-BENZYLALCOHOLS

[75] Inventors: Yuzuro Yamamoto, Kanazawa; Hideo Kato, Katsuyama Fukui; Sakae Kurata, Katsuyama Fukui; Kazunori Nishide, Katsuyama Fukui, all of Japan

[73] Assignee: Hokuriku Pharmaceutical Co., Ltd., Fukui, Japan

[22] Filed: May 5, 1975

[21] Appl. No.: 575,052

[30] Foreign Application Priority Data

May 16, 1974 Japan .............................. 49-53903

[52] U.S. Cl. ................... 260/501.17; 260/570.5 C; 260/570.6; 260/592; 424/316; 424/330
[51] Int. Cl.² ....................................... C07C 91/22
[58] Field of Search .................... 260/570.6, 501.17

[56] References Cited

UNITED STATES PATENTS 3,714,229 1/1973 Saari et al. ................ 260/570.6 X
3,732,300 5/1973 Lunts et al. ................ 260/570.6 X

*Primary Examiner*—Robert V. Hines
*Attorney, Agent, or Firm*—Burgess Ryan and Wayne

[57] ABSTRACT

Hydroxyl-substituted-2-chloro-α-(Tert-butylaminomethyl)-benzylalcohols of the formula:

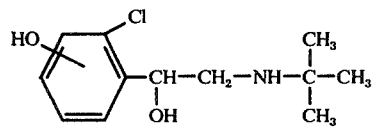

and process for their production are disclosed. These compounds are useful as bronchodilators.

4 Claims, No Drawings

HYDROXYL-SUBSTITUTED 2-CHLORO-α-(TERT-BUTYLAMINOMETHYL)-BENZYLALCOHOLS

This invention relates to hydroxyl-substituted 2-chloro-α-(tert-butylaminomethyl)-benzylalcohols of the general formula

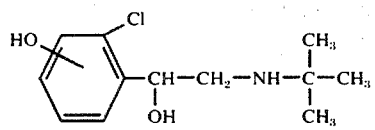

(I)

and a process for their production.

The compounds of this invention are useful as a medicine because of their bronchodilator activity.

According to the present invention, the above compounds are produced in two main steps:
1. a step for the preparation of hydroxyl-substituted 2-chloro-phenylglyoxal derivatives by oxidation of hydroxyl-substituted 2-chloroaceto-phenone derivatives with selenium dioxide, and
2. a step for the preparation of hydroxyl-substituted 2-chloro-α-(tert-butylaminomethyl)-benzylalcohols by reduction of the hydroxyl-substituted 2-chlorophenylglyoxal derivatives in the presence of tert-butylamine.

The process of this invention is shown according to the following chemical scheme:

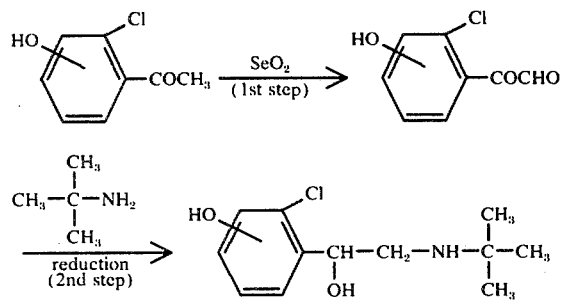

In the first step hydroxyl-substituted 2-chloroacetophenone derivatives are oxidized in water or in an organic solvent with selenium dioxide at equimolar quantity or at an excess, to obtain hydroxyl-substituted 2-chlorophenylglyoxal derivatives. As an organic solvent, alcohols, e.g. methanol, ethanol etc. acetic acid, dioxane or their mixtures, preferably dioxane are suitable. The reaction is desirably carried out at about the boiling points of the solvents employed.

In the second step the thus obtained hydroxyl-substituted 2-chlorophenylglyoxal derivatives are reduced in the presence of tertbutylamine at an equimolar quantity or at an excess in an organic solvent such as a methanol, ethanol etc. with reducing agents such as a metal borohydride complex for example sodium- or potassium borohydride etc. to form the desired hydroxyl-substituted 2-chloro-α-(tert-butylaminomethyl)-benzylalcohols of this invention. As an organic solvent, alcohols such as methanol, ethanol etc., cyclic ethers such as tetrahydrofuran, dioxan etc., acetates such as methyl acetate, ethyl acetate, etc., or dimethylsulfoxide or dimethylformamide etc. may be mentioned.

The reaction temperature ranges from 0° C to about the boiling point of the solvent employed, preferably 0° – 10° C.

As the compounds of this invention have an asymmetric carbon atom in their molecules, they are optical active and can be separated into isomers in the usual manner.

The dosage in oral administration is 1 – 5 mg, preferably 2 – 4 mg, three times a day.

The compounds of this invention can be administered not only per os., but also in the form of suppository, spray etc.

The present invention is further illustrated by the following examples.

EXAMPLE 1:

2-Chloro-5-hydroxyphenylglyoxal

To a solution at 50° – 60° C of selenium dioxide (0.83 g) in dioxane (4.5 ml) and water (0.15 ml) was added 2-chloro-5-hydroxyacetophenone (0.85 g), and the reaction mixture was refluxed with stirring for 4 hours. The deposited selen was filtered, and the filtrate was evaporated. The residue was dissolved in ether, the ether-layer was washed with water, dried with $Na_2SO_4$ and evaporated. The residue (0.51 g) was used to the following process.

EXAMPLE 2:

2-Chloro-5-hydroxy-α-(tert-butylaminomethyl)-benzylalcohol

To a solution of 2-chloro-5-hydroxyphenylglyoxal (1.85 g) in methanol (37 ml) was added a solution of tert-butylamine (3.65 g) in methanol under cooling, further the sodium borohydride (0.57 g) was added in small portions, and the reaction mixture was stirred for 3 hours. The reaction mixture was evaporated and the residue acidified with 10% HCl, and washed with ether. The aqueous layer was made alkaline with $K_2CO_3$, and extracted with ether. The extract was dried with $Na_2SO_4$ and evaporated. The residue was recrystallized from iso-propylether n-hexane to give a 2-chloro-5-hydroxy-α-(tert-butylaminomethyl)-benzylalcohol, m.p. 162° – 163° C. Hydrochloride: m.p. 245° – 248° C.

The following compounds were obtained in a similar manner.

i. 2-Chloro-3-hydroxy-α-(tert-butylaminomethyl)-benzylalcohol oxalate, m.p. 240° – 243° C.

ii. 2-Chloro-4-hydroxy-α-(tert-butylaminomethyl)-benzylalcohol oxalate, m.p. 165° – 168° C.

What is claimed is:

1. A hydroxyl-substituted 2-chloro-α-(tert-butylaminomethyl)-benzylalcohol of the general formula

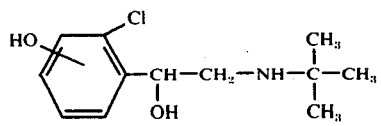 (I)

and salts thereof.

2. 2-Chloro-4-hydroxy-α-(tert-butylaminomethyl)-benzylalcohol and its oxalate.

3. A hydroxyl-substituted 2-chloro-α-(tert-butylamino-methyl)-benzylalcohol according to claim 1 which is 2-chloro-3-hydroxy-α-(tert-butylaminomethyl)-benzylalcohol and its oxalate.

4. A hydroxyl-substituted 2-chloro-α-(tert-butylamino-methyl)-benzylalcohol according to claim 1 which is 2-chloro-4-hydroxy-α-(tert-butylaminomethyl)-benzylalcohol and its oxalate.

* * * * *

UNITED STATES PATENT OFFICE
CERTIFICATE OF CORRECTION

Patent No. 4,018,818   Dated April 19, 1977

Inventor(s) Yuzuru Yamamoto, et al

It is certified that error appears in the above-identified patent and that said Letters Patent are hereby corrected as shown below:

In the Title Page:

Under "Inventors", the primary inventor's name should read --Yuzuru Yamamoto--.

Under "Inventors", the addresses should read, respectively:
      --Kanazawashi Ishikawa
        Katsuyamashi Fukui
        Katsuyamashi Fukui
        Katsuyamashi Fukui--.

Column 1, line 60:  Change "reducing agents" to --a reducing agent--.

Column 2, line 5:  Change "optical" to --optically--.

line 23:  Change "selen" to --selenium--.

Signed and Sealed this

Eighteenth Day of October 1977

[SEAL]

Attest:

RUTH C. MASON
Attesting Officer

LUTRELLE F. PARKER
Acting Commissioner of Patents and Trademarks